United States Patent [19]

Karrer et al.

[11] 4,429,077
[45] Jan. 31, 1984

[54] PROCESS FOR CURING STOVING LACQUERS

[75] Inventors: Friedrich Karrer, Zofingen; Godwin Berner, Rheinfelden; Jean Rody, Riehen, all of Switzerland

[73] Assignee: Ciba-Geigy Corporation, Ardsley, N.Y.

[21] Appl. No.: 328,885

[22] Filed: Dec. 9, 1981

[30] Foreign Application Priority Data

Dec. 19, 1980 [CH] Switzerland .................. 9408/80

[51] Int. Cl.³ ............... B01J 31/02; C08L 33/00; C08L 61/06; C08L 61/28
[52] U.S. Cl. .................. 525/143; 525/157; 525/176; 525/329.8; 525/329.9; 525/330.4; 525/330.5; 525/375; 525/504; 525/509; 502/167
[58] Field of Search ............ 252/438, 426; 525/157, 525/143, 330.4, 330.5, 176, 329.8, 329.9, 375, 504, 509

[56] References Cited

U.S. PATENT DOCUMENTS 3,474,054 10/1969 White .................. 260/15

FOREIGN PATENT DOCUMENTS 2753 7/1979 European Pat. Off. .
6213 11/1979 European Pat. Off. .
2920306 11/1979 Fed. Rep. of Germany .

*Primary Examiner*—Allan Lieberman
*Attorney, Agent, or Firm*—Harry Falber

[57] ABSTRACT

Acid addition salts of basic polyalkylpiperidine derivatives, which contain a group of the formula I

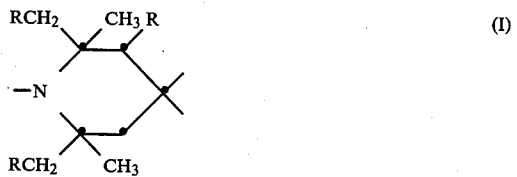

in which R is H or $CH_3$, and an inorganic or organic acid, and also inner salts of sulfonic acids which contain a group of the formula I, are suitable as curing catalysts for acid-curable stoving lacquers. Their advantage is a long pot life and also an additional light stabilizing action.

10 Claims, No Drawings

PROCESS FOR CURING STOVING LACQUERS

The invention relates to a process for curing acid-curable stoving lacquers using acid addition salts of basic polyalkylpiperidine derivatives or inner salts of polyalkylpiperidinesulfonic acids.

Stoving lacquers are lacquers which can be cured by heat treatment. They are based on binders which are able to enter into crosslinking reactions on stoving. Such binders can be, for example, acrylic resins, polyester resins, alkyd resins, phenolic resins, melamine resins, urea resins, epoxide resins or polyurethane resins. The binders can also be mixtures of two different resins, for example of a polyester resin and a melamine resin, or mixtures of a reactive resin and a monomeric crosslinking agent, for example an acrylic resin with a glycol diacrylate, or resins which in themselves contain different reactive groups, for example acrylate-modified polyesters. The reactive groups capable of crosslinking can be olefinic double bonds which crosslink with copolymerisation, or groups which are capable of polycondensation. The latter groups dominate in the stoving lacquers customarily used nowadays, and, despite different chemical curing mechanisms, a common feature of these polycondensation resins is that curing thereof can be accelerated by acid catalysts. The advantage of adding curing catalysts is that the curing times required are shortened or the curing temperatures required are lowered. The disadvantage of adding the catalyst is that the storage stability is reduced, since in the presence of such catalysts slow polycondensation already starts at room temperature. The acid catalyst can thus be added to the lacquer only shortly before the latter is applied, and the lacquer catalysed in this way must be applied within specific pot lives. For this reason, curing catalysts are used only in specific cases, for example in automobile repair lacquers, where stoving at high temperatures is not possible.

The acid catalysts used in these cases are acids of low volatility, for example phosphoric acid, aromatic sulfonic acids or maleic acid half-esters. It has also already been proposed to use salts of the acids with organic amines, in place of the free acids. For example, U.S. Pat. No. 3,474,054 proposes pyridine salts of p-toluene-sulfonic acid and German Offenlegungsschrift No. 2,920,306 proposes oxazolidine salts of aromatic sulfonic acids as curing catalysts. Such salts are approximately neutral at room temperature; on heating, the volatile amine is split off and the non-volatile acid remains in the lacquer, where it effects rapid curing. Salts of this type can therefore be designated latent acid curing catalysts. The advantage of these salts is that the pot life is considerably prolonged, but the disadvantage of these salts is a troublesome odour during the curing process, due to the volatilising amine. Since amines are not physiologically acceptable, the stoving equipment must be fitted with efficient extractors and the air mixture drawn off must be purified. There is, therefore, a need for latent curing catalysts which do not release amine vapours on stoving and nevertheless ensure long pot lives.

It has been found that acid addition salts of amines which are of low volatility or are non-volatile can also be used as curing catalysts. Thus, it is possible to use salts of those amines which are known as light stabilisers, for example salts of derivatives of polyalkylpiperidines. Since these amines do not volatilise during the stoving process, they remain as a light stabiliser in the lacquer.

Thus, such salts act, by reason of their acid anion, as curing catalysts for acid-curable lacquer resins and, by reason of their cation, as light stabilisers for the cured lacquers.

The invention therefore relates to a process for curing stoving lacquers by warming in the presence of a curing catalyst, wherein the curing catalyst used is either (a) an acid addition salt of a basic polyalkylpiperidine derivative which contains a group of the formula I

in which R is hydrogen or methyl, and an inorganic or organic acid, or (b) the inner salt of a sulfonic acid which contains a group of the formula I. In formula I, R is preferably hydrogen.

Stoving lacquers suitable for this purpose are those stoving lacquers with which curing can be accelerated by means of acid catalysts. These are, in particular, lacquers based on acrylic, polyester, alkyd, melamine and phenolic resins, but in particular the mixtures of acrylic, polyester or alkyd resins with one another or with a melamine resin. These also include modified lacquer resins, for example acrylic-modified polyester or alkyd resins. Examples of individual types of resin which fall under the term acrylic, polyester and alkyd resins are described, for example, in Wagner and Sarx-/Lackkunstharze (Synthetic Lacquer Resins) (Munich, 1971) on pages 86–123 and 229–238, or in Ullmann/Encyclopädie der techn. Chemie (Encyclopaedia of Industrial Chemistry), 4th edition, volume 15 (1978), pages 613–628. Acid catalysts is of particular importance for the curing of lacquers which contain etherified melamine resins, for example methylated or butylated melamine resins (N-methoxymethyl- and N-butoxymethylmelamines).

Polyalkylpiperidine derivatives which contain the group of the formula I are known as light stabilisers. They can be mono-, oligo- or poly-piperidines, depending on whether the compounds contain one or more groups of the formula I in their molecule or whether the compounds are polymers with recurring units of the formula I. Most of these piperidine derivatives contain a polar substituent, for example an ether, ester, amide, carbamate, ketal, amino or triazinyl group, in the 4-position of the piperidine derivative. The categories of polyalkylpiperidines which are the most important and are preferred according to the invention are the following compound categories: (a) 4-hydroxypiperidines and their ethers, esters and carbamates of the formula

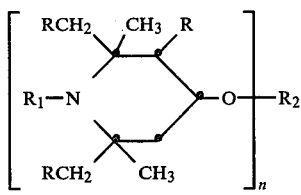

in which R is hydrogen or methyl, $R_1$ is alkyl, hydroxyalkyl, cyanoalkyl, alkenyl, alkynyl or aralkyl, preferably $C_1$–$C_4$-alkyl, allyl or benzyl, n is 1 to 4, preferably 1 or 2, and $R_2$, if n is 1, is hydrogen, alkyl, cyanoethyl, benzyl, glycidyl, a monoacyl radical of a saturated or unsaturated aliphatic, cycloaliphatic, araliphatic or aromatic mono- or di-carboxylic acid, carbamic acid or phosphorus-containing acid or a monovalent silyl radical, preferably a radical of an aliphatic monocarboxylic acid having 2 to 18 C atoms or of an aromatic monocarboxylic acid having 7 to 15 C atoms, or $R_2$, if n is 2, is alkylene, alkenylene, xylylene, a diacyl radical of a saturated or unsaturated aliphatic, cycloaliphatic, araliphatic or aromatic dicarboxylic acid, dicarbamic acid or phosphorus-containing acid or a divalent silyl radical, preferably a radical of an aliphatic dicarboxylic acid having 4–14 C atoms, of an aromatic dicarboxylic acid having 8–14 C atoms or of an aliphatic, cycloaliphatic or aromatic dicarbamic acid having 8–14 C atoms, or $R_2$, if n is 3, is a triacyl radical of an aliphatic, cycloaliphatic or aromatic tricarboxylic acid, of an aromatic tricarbamic acid or of a phosphorus-containing acid or a trivalent silyl radical, and $R_2$, if n is 4, is a tetraacyl radical of an aliphatic, cycloaliphatic or aromatic tetracarboxylic acid.

(b) 4-Aminopiperidines and their N-acyl derivatives of the formula

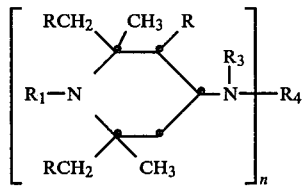

in which n is the number 1 or 2, R and $R_1$ are as defined under (a), $R_3$ is alkyl, cycloalkyl, aralkyl, alkanoyl, alkenoyl or benzoyl and $R_4$, if n is 1, is alkyl, cycloalkyl, alkenyl, which is unsubstituted or substituted by a cyano, carbonyl or carbamide group, or glycidyl or a group of the formula —$CH_2$—$CH(OH)$—Z, in which Z is hydrogen, methyl or phenyl, or $R_3$ and $R_4$ together are the cyclic radical of an aliphatic or aromatic 1,2- or 1,3-dicarboxylic acid, and, if n is 2, $R_4$ is alkylene, xylylene, a —$CH_2$—$CH(OH)$—$CH_2$ group or a —$CH_2$CH(OH)—$CH_2$—O—X—O—$CH_2$—$CH(OH)$— group, in which X is alkylene, arylene or cycloalkylene or, with the proviso that $R_3$ is not alkanoyl, alkenoyl or benzoyl, $R_4$ can also be a divalent radical of an aliphatic, cycloaliphatic or aromatic dicarboxylic acid or dicarbamic acid.

(c) Cyclic ketals of 4-oxopiperidines of the formula

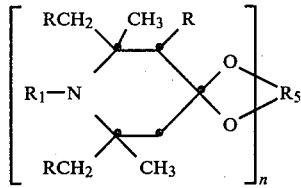

in which n is the number 1 or 2, R and $R_1$ are as defined under (a) and $R_5$, if n is 1, is alkylene or hydroxyalkylene or acyloxyalkylene and, if n is 2, is the group (—$CH_2$)$_2$C($CH_2$—)$_2$.

(d) Spirohydantoins of the formula

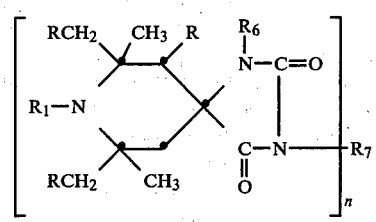

in which n is 1 or 2, R and $R_1$ are as defined under (a), $R_6$ is hydrogen, alkyl, allyl, benzyl, glycidyl or alkoxyalkyl and $R_7$, if n is 1, is hydrogen, alkyl, glycidyl, alkenyl, aralkyl, cycloalkyl, hydroxyalkyl, alkoxyalkyl or aryl and, if n is 2, is alkylene, arylene or a —$CH_2$—$CH(OH)$—$CH_2$—O—X—O—$CH_2$—$CH(OH)$—$CH_2$— group, in which X is as defined under (b).

(e) Triazine derivatives of the formula

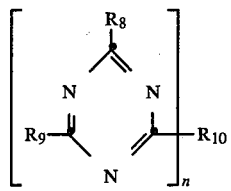

in which n is 1, 2 or 3 and $R_8$ is a group of the formula

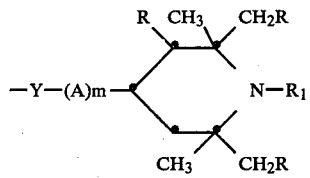

in which R and $R_1$ are as defined under (a), Y is —O— or —$NR_{11}$—, A is alkylene and m is 0 or 1, $R_9$ has the meaning defined for $R_8$ or is one of the groups —$NR_{11}R_{12}$ or —$OR_{13}$, $R_{10}$, if n is 1, has the meaning defined for $R_8$ or $R_9$, and if n is 2 is a —Y—Q—Y— group, in which Q is alkylene which can be interrupted by —O— or —$N(R_{14})$—, and if n is 3 is an

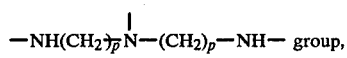

in which p is 2 or 3, $R_{11}$ is alkyl, cyclohexyl, benzyl or hydroxyalkyl or a group of the formula

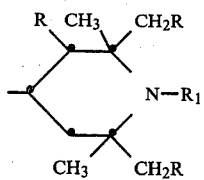

and $R_{12}$ is alkyl, cyclohexyl, benzyl or hydroxyalkyl, or $R_{11}$ and $R_{12}$ together are $C_4$–$C_5$-alkylene or oxa-alkylene, or $R_{11}$ and $R_{12}$ are each a group of the formula

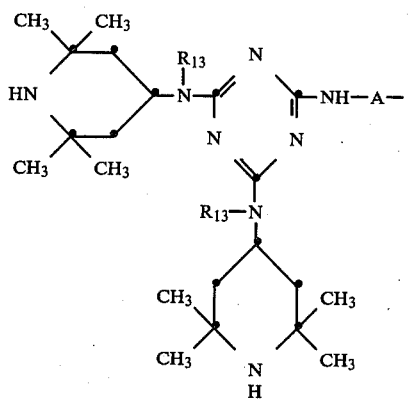

$R_{13}$ is hydrogen, alkyl or phenyl and $R_{14}$ is hydrogen or $C_1$–$C_4$ alkyl.

(f) Spirooxazolidones of the formula

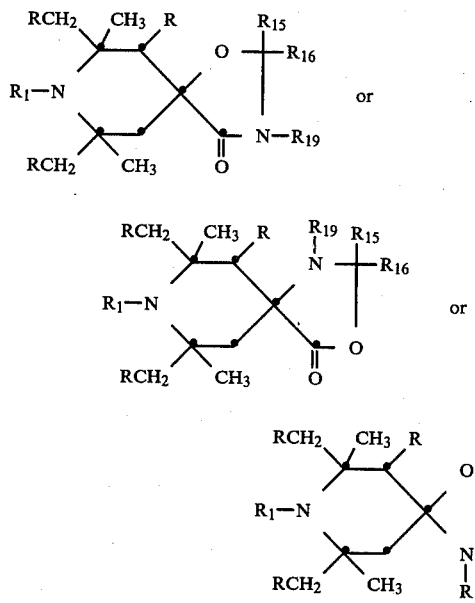

in which R and $R_1$ are as defined under (a) and $R_{15}$ and $R_{16}$ independently of one another are hydrogen, alkyl, aryl, aralkyl or cycloalkyl, or $R_{15}$ and $R_{16}$ together are $C_4$–$C_{11}$-alkylene, and $R_{19}$ is hydrogen, alkyl, allyl or benzyl.

(g) Bis-piperidines of the formula

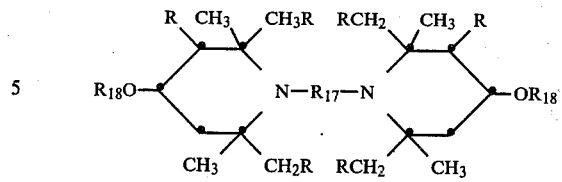

in which $R_{17}$ is alkylene, alkenylene or aralkylene, preferably but-2-en-1,4-ylene or p-xylylene, and $R_{18}$ is hydrogen, allyl, benzyl or a —CO—$R_{19}$ or —CO—$R_{20}$—COOH group, in which $R_{19}$ is alkyl, aryl or cyclohexyl and $R_{20}$ is alkylene or alkenylene.

(h) Polymeric compounds in which the recurring structural units contain a group of the formula I and this can be a recurring constituent of the main chain of the polymer or a constituent of a recurring side group, in particular polyesters, polyethers, polyamides, polyamines, polyurethanes, polyureas, polyaminotriazines, poly(meth)acrylates, poly(meth)acrylamides and their copolymers which contain such radicals.

Preferred acid addition salts of polyalkylpiperidine derivatives are those which contain a group of the formula Ia,

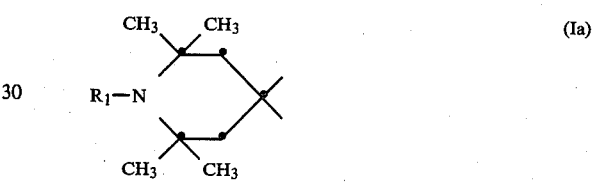

(Ia)

in which $R_1$ is $C_1$–$C_4$-alkyl, cyanomethyl, $C_3$–$C_5$-alkenyl or $C_7$–$C_9$-aralkyl, in particular allyl or benzyl.

Examples of acids which form salts, in the sense according to the invention, with the piperidine derivatives are inorganic acids, for example phosphoric acid or amidosulfonic acid, but preferably organic acids, such as mono- or poly-sulfonic acids, for example methanesulfonic acid, methylamidosulfonic acid, ethanesulfonic acid, 2-ethylhexanesulfonic acid, vinylsulfonic acid, benzenesulfonic acid, toluene- or naphthalene-sulfonic acids, benzene- or naphthalene-disulfonic acids, styrenesulfonic acid, alkylated benzene- or naphthalene-sulfonic acids, industrial mixtures of paraffinsulfonic acids, acrylamido-N-alkanesulfonic acids, polystyrenepolysulfonic acids or polyvinylsulfonic acid; acid phosphoric acid esters, for example phenylphosphoric acid or diethylphosphoric acid; phosphonic and phosphinic acids, for example methylphosphonic acid, phenylphosphonic acid, dodecylphenylphosphonic acid, phenyl-butyl-phosphinic acid, diphenylphosphinic acid or methyl-benzyl-phosphinic acid; phosphonic acid monoesters, for example methyl methylphosphonate or ethyl phenylphosphonate; maleic acid and its monoesters, for example monobutyl maleate or monohexyl maleate; and phthalic acid and its monoesters, for example monohexyl phthalate or monooctyl phthalate.

Preferred salts are those of mono- and poly-sulfonic acids, of acid phosphoric acid esters, of phosphonic acids and their monoesters, of maleic acid and its monoesters and of phthalic acid and its monoesters.

Particularly preferred acid addition salts are those of polyalkylpiperidine derivatives, which contain a group of the formula I, in which R is hydrogen, with a mono- or di-sulfonic acid.

The salts can be neutral salts, i.e. they contain exactly the same number of base equivalents as of acid equivalents. However, these salts can also be acid or basic salts, that is to say salts in which either the acid equivalents or the basic equivalents are in excess. Neutral salts or salts with a small excess (1–20%) of base equivalents are preferred.

A certain basicity of the salts, such as results in the case of an excess of base equivalents, is of advantage for a high storage stability of the lacquers catalysed with these salts. However, an excess of base is a disadvantage for rapid heat-curing. Therefore, the basicity can be varied correspondingly, depending on the intended use of the lacquers. The basicity can be increased not only by using the piperidine base, on which the salt is based, in excess; it is also possible to increase the basicity of the curing catalyst by the addition of small amounts of other amine bases and thus to increase the storage stability of the lacquer.

The salts can be prepared in a known manner by neutralising the piperidine base with an acid. This is preferably effected by mixing solutions of the two components. If the salt is insoluble or sparingly soluble in the solvent used, it precipitates or crystallises out from the solution. If this is not the case, the salt is isolated by evaporating the solvent. However, for use, according to the invention, for curing lacquers, the resulting solutions can also be used, or the solution is concentrated to a specific concentration by distilling off some of the solvent.

As organic salts, these piperidine salts are soluble not only in water but also in organic solvents. This is important for their use in lacquers, since these usually contain organic solvents. The solubility of the salts depends on their constitution, in particular on the nature of the acid radical (anion). The same applies in the case of the consistency of the salts. These can be oily syrups or low-melting amorphous solids or higher-melting crystalline solids. If they are solids, they do not have a sharp melting point, since they partly dissociate into base and acid on heating and a partial softening of the salt can be observed at its melting point.

At room temperature, the majority of the salts are in the protonated form. With the aid of an individual compound, this can be expressed, by way of example, by the following two formulae:

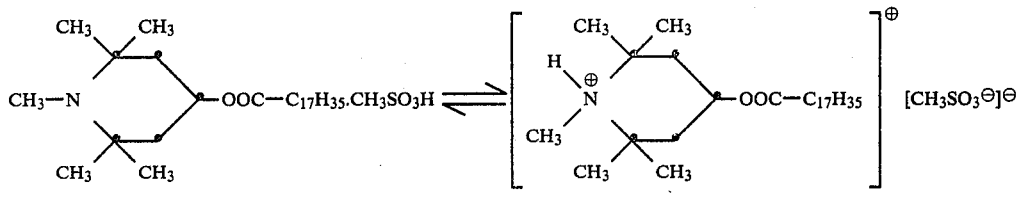

If the more simple nomenclature according to the formula on the left is used in the text which follows, this nevertheless signifies that the bulk of the salt can be in the form of the right hand formula.

Examples of acid addition salts of polyalkylpiperidines which can be used according to the invention are the compounds of the following formulae, in which

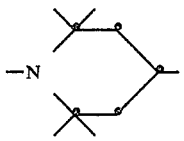

is intended to denote a radical of the formula

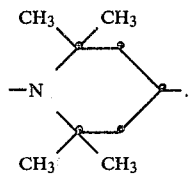

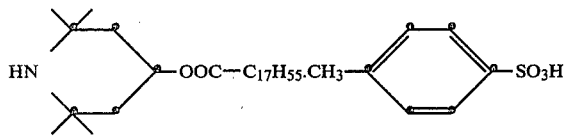

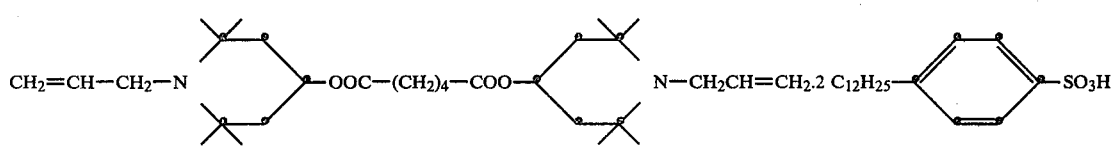

-continued
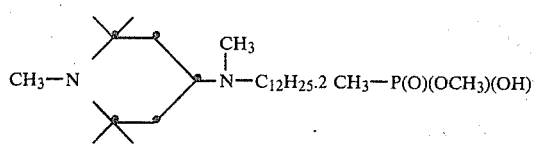
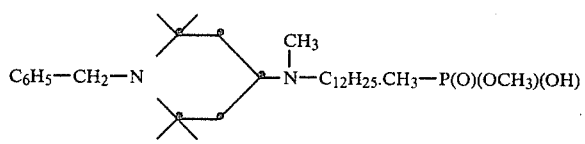
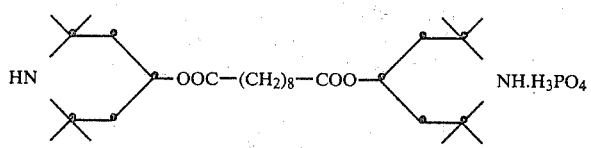
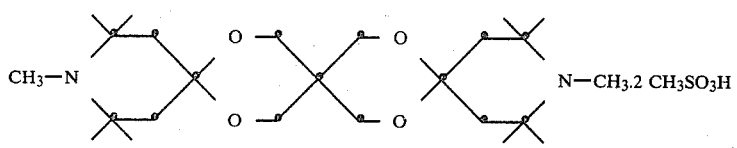
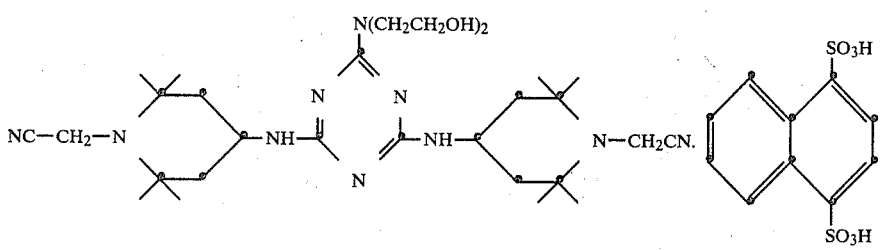
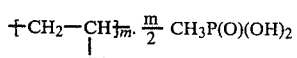
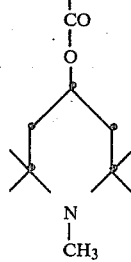
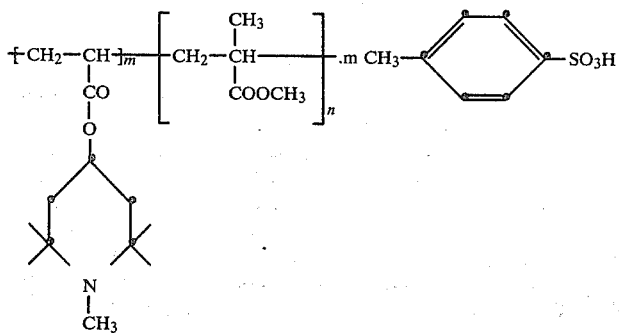

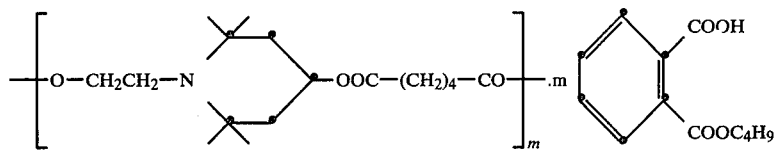

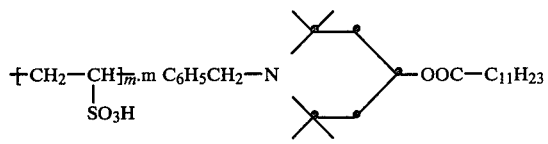

In place of these acid addition salts it is also possible to use inner salts of sulfonic acids which contain a group of the formula I, in particular of sulfonic acids of the following general formulae Amongst the salts, the inner salts of sulfonic acids of the formula II in which $R^1$ is methyl, allyl or benzyl and $R^2$ is a —(CH$_2$)$_3$— group are preferred.

Some of these inner salts of polyalkylpiperidinesul-

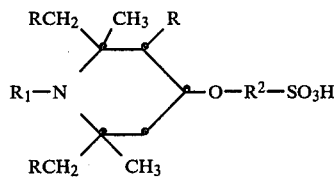

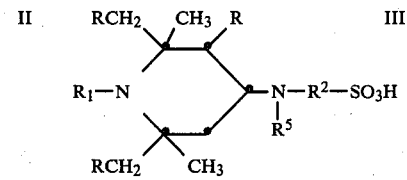

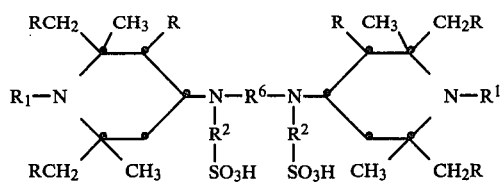

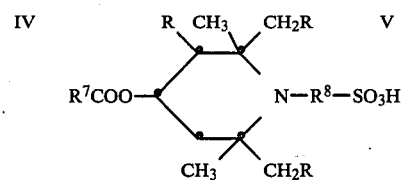

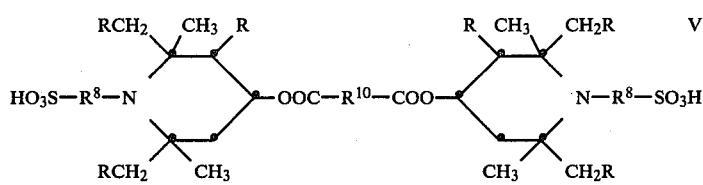

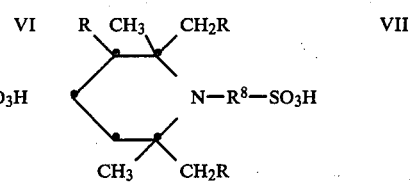

in which R is hydrogen or methyl, $R^{1'}$ is hydrogen, $C_1$-$C_{12}$ alkyl, $C_3$-$C_8$ alkenyl, $C_3$-$C_8$ alkynyl, $C_7$-$C_{12}$ aralkyl or —CH$_2$CN, $R^2$ is a —(CH$_2$)$_3$— or —CH$_2$—CH($R^3$)—CONH-$R^4$ group, in which $R^3$ is hydrogen or methyl and $R^4$ is $C_2$-$C_8$ alkylene, $R^5$ is $C_1$-$C_{12}$ alkyl, fonic acids are in a so-called betain form, in which the proton of the acid group is located on the basic nitrogen atom. An equilibrium exists between the two limiting forms and this can be represented as follows, using a specific compound as an example:

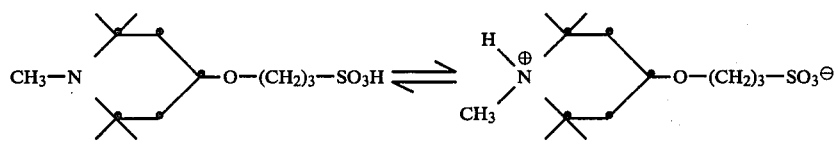

$C_5$-$C_7$ cycloalkyl or $C_7$-$C_9$ aralkyl, $R^6$ is $C_2$-$C_{12}$ alkylene, $C_4$-$C_{10}$ alkylene which is interrupted by —O—, $C_6$-$C_{15}$ cycloalkylene or xylylene, $R^7$ is $C_1$-$C_{18}$ alkyl, $C_6$-$C_{12}$ aryl or alkaryl, $C_7$-$C_{12}$ aralkyl or a $R^{11}$—NH—, $R^8$ is —(CH$_2$)$_3$— or —CH$_2$—CH($R^9$)—O—(CH$_2$)$_3$—, $R^9$ is hydrogen, methyl, phenyl, phenoxymethyl or tolyloxymethyl, $R^{10}$ is $C_2$-$C_{12}$ alkylene, $C_2$-$C_{12}$ alkylene interrupted by —O—, $C_6$-$C_{12}$ arylene, $C_6$-$C_{12}$ cycloalkylene or an —NH—$R^{12}$—NH— group, $R^{11}$ is $C_1$-$C_{18}$ alkyl, cyclohexyl, $C_6$-$C_{12}$ aryl or $C_7$-$C_9$ aralkyl and $R^{12}$ is $C_2$-$C_{12}$ alkylene, $C_6$-$C_{14}$ arylene or $C_6$-$C_{12}$ cycloalkylene.

The position of the equilibrium depends on the nature of the solvent and on the temperature.

The polyalkylpiperidinesulfonic acids of the formulae II to VII are novel compounds, which as well as being used as curing catalysts for lacquers can also be used as light stabilisers for diverse organic materials, for example for plastics, cosmetics or photographic layers.

The compounds of the formulae II to IV, in which $R^2$ is a —(CH$_2$)$_3$— group, can be prepared by reacting the corresponding piperidines, which possess an OH or NH group in the 4-position, with propanesultone, for example in accordance with the following equation, for compounds of the formula II:

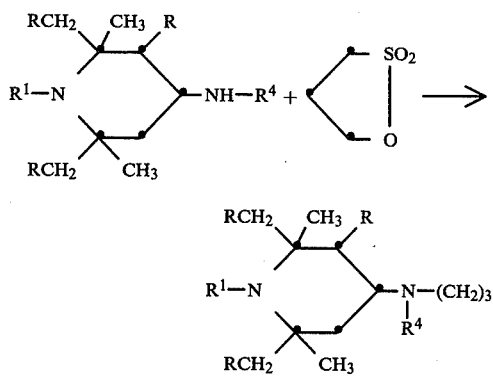

If $R^2$ is a group of the formula —$CH_2$—$CH(R^3)$—$CONH$—$R^4$ in the compounds of the formulae II-IV, these compounds can be prepared from the corresponding OH or NH compounds by reaction with a (meth)acrylamido-alkylsulfonic acid of the formula VIII $$CH_2=C(R^3)—CONH—R^4—SO_3H \qquad VIII$$

Compounds of the formula V to VII in which $R^8$ is a —$(CH_2)_3$— group can be prepared from the corresponding piperidines which are unsubstituted in the 1-position, by reaction with propanesultone, for example in accordance with the following equation for compounds of the formula V:

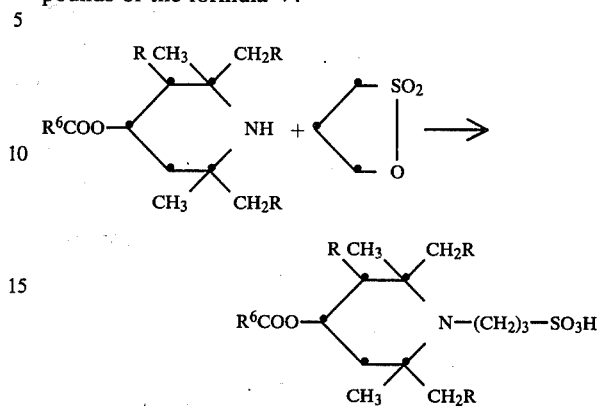

The compounds of the formulae V to VII in which $R^8$ is a —$CH_2$—$CH(R^9)$—$O$—$(CH_2)_3$— group can be prepared analogously, by reacting the corresponding 1-hydroxyalkylpiperidines with propanesultone.

Examples of polyalkylpiperidinesulfonic acids which can be used according to the invention are the compounds of the formulae given below, in which

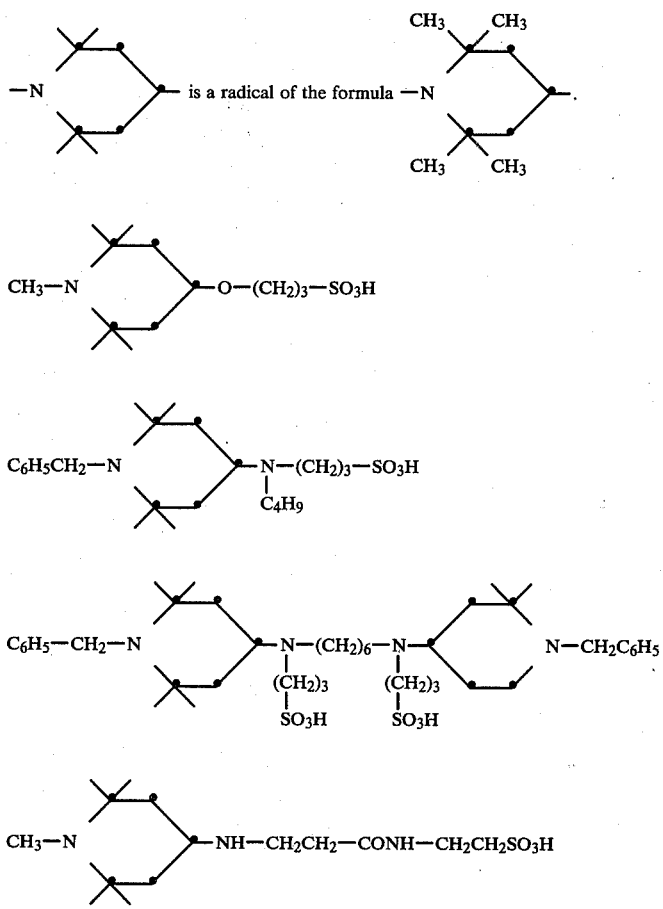

-continued

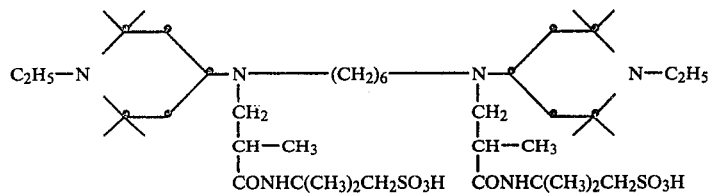

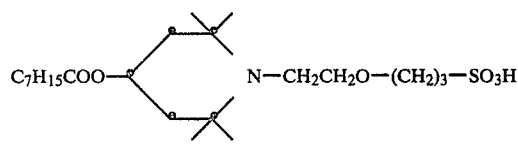

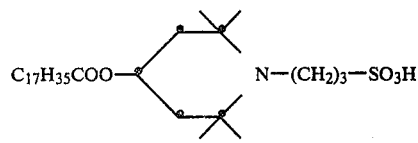

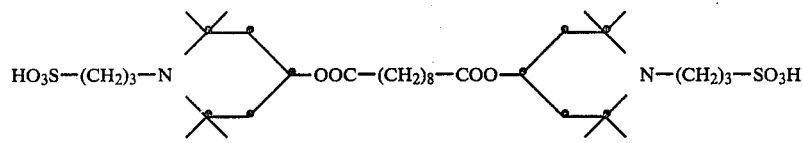

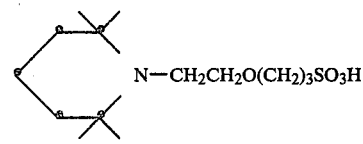

In the text which follows, the preparation of acid addition salts of polyalkylpiperidine derivatives and also of inner salts of polyalkylpiperidinesulfonic acids by various methods is described by way of example, and individual salts prepared in this way are described. In these examples the temperatures are in °C.

Preparation of acid addition salts—method A 12.6 g (0.025 mol) of di-(1-allyl-2,2,6,6-tetramethyl-4-piperidyl) adipate, dissolved in 125 ml of acetonitrile, are mixed with a solution of 9.5 g (0.05 mol) of p-toluenesulfonic acid monohydrate in 70 ml of acetonitrile, the solvent is distilled off in vacuo and the residue is crystallised from ethylene glycol dimethyl ether. The crystals are filtered off, washed with a little hexane and dried in vacuo. The resulting salt of the formula

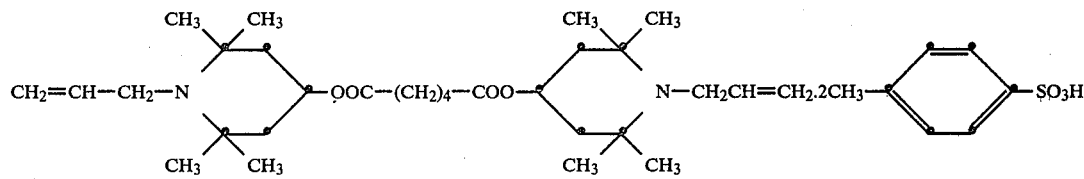

melts at 196°–197° C.

Method B

A solution of 9.63 g of di-(1,2,2,6,6-pentamethyl-4-piperidyl) sebacate in 50 ml of methylene chloride is mixed with a solution of 11.84 g of technical grade dodecylbenzenesulfonic acid (equivalent weight 329) in 100 ml of hexane. The resulting solution is evaporated in vacuo and the syrupy residue is dissolved in 20.6 g of xylene, a 50% solution of the salt of the formula

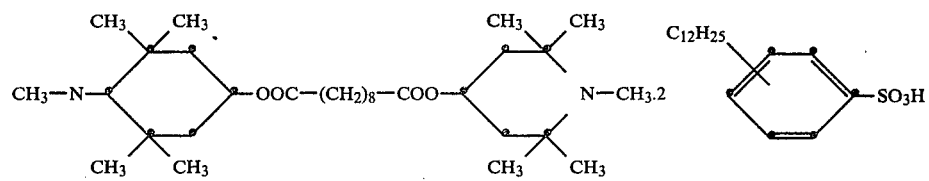

being obtained by this means.

Method C

A solution of 11.5 g (0.02 mol) of di-(1-allyl-2,2,6,6-tetramethyl-4-piperidyl) sebacate in 100 ml of acetone is mixed with 19.1 g (0.02 mol) of a 50% solution of technical grade dinonylnaphthalenedisulfonic acid in isobutanol (titrated equivalent weight of the solution 478), with stirring. The resulting turbid solution is filtered and the filtrate is evaporated to dryness in vacuo. The salt of the formula

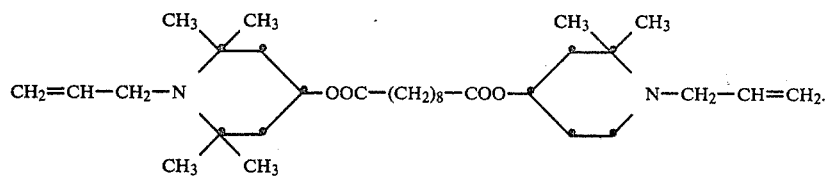

which is thus obtained is a yellowish powder which softens at 104° C.

Salts prepared analogously

The list which follows describes salts which have been prepared by the methods describes above. The following abbreviations are used:

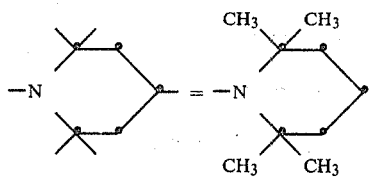

TSA = p-toluenesulfonic acid

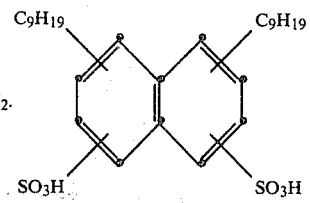

MPA = methylphosphonic acid $CH_3-P(O)(OH)_2$
MMP = methyl methylphosphonate $CH_3-P(O)-(OCH_3)(OH)$
DBA = 4-dodecylbenzenesulfonic acid
MSA = mesitylenesulfonic acid
PSA = technical grade $C_{14}-C_{17}$ paraffinsulfonic acid (equivalent weight 282)
DNND = technical grade dinonylnaphthalenedisulfonic acid
NND = technical grade nonylnaphthalenedisulfonic acid

| Salt No. | Formula | Softening or melting point |
|---|---|---|
| 1 | CH₃—N⟨piperidyl⟩—OH.MMP | 90° |
| 1a | .½ MPA | 170° |
| 1b | .½ DNND | 250° |
| 2 | CH₂=CH—CH₂—N⟨piperidyl⟩—OH.MMP | Oil |
| 2a | .½ MPA | 80° |
| 3 | C₆H₅—CH₂—N⟨piperidyl⟩—OH.MPA | 140° |
| 3a | .½ MPA | 40° |
| 3b | . MMP | 70° |
| 4 | HOCH₂CH₂—N⟨piperidyl⟩—OH.TSA | 132 to 134° |
| 4a | .½ DNND | 98° |

-continued
| Salt No. | Formula | Softening or melting point |
|---|---|---|
| 5 | 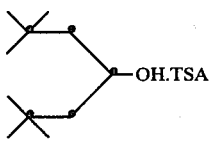 | 152° |
| 6 | 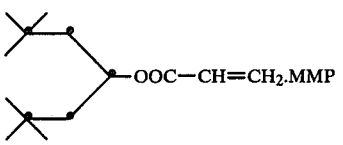 | Syrup |
| 6a | .C₄H₉OOC—CH=CH.COOH | oil |
| 6b | .DBA | 94–99° |
| 6c | .TSA | 115° |
| 6d | .CH₃SO₃H | 190° |
| 6e | .½ DNND | 69° |
| 7 | 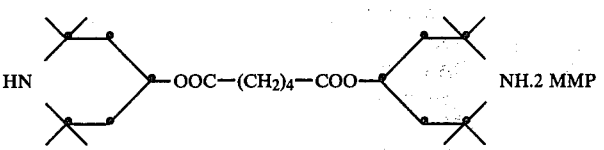 | 145° |
| 8 | 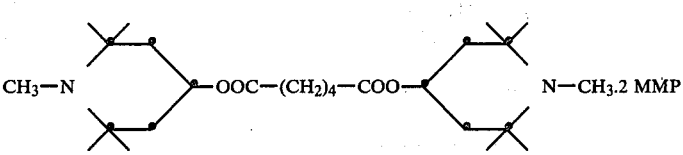 | oil |
| 9 | 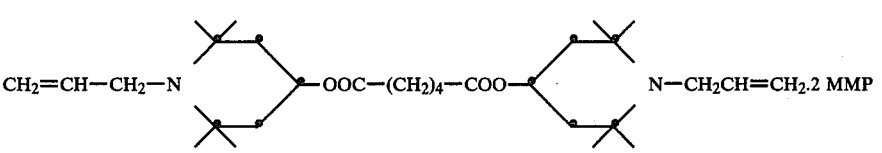 | 30° |
| 9a | .2 MPA | 30° |
| 9b | .2 TSA | 196° |
| 9c | .DNND | 120° |
| 9d | .2 DBA | 95° |
| 9e | .NND | oil |
| 10 | 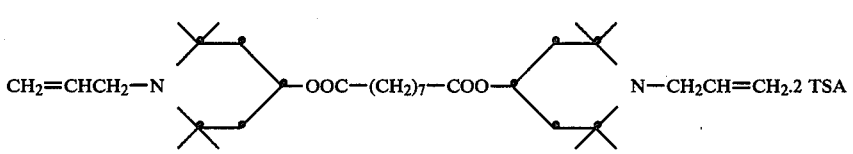 | oil |
| 10a | .MPA | Oil |
| 10b | .2 MMP | liquid |
| 10c | .2 MSA | 75° |
| 10d | 2 PSA | Oil |
| 10e | 2 CH₃SO₃H | 62° |
| 10f | 2 C₂H₅—SO₃H | 52° |
| 10g | 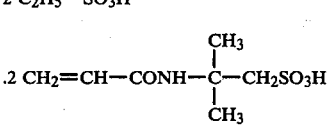 | 56° |
| 10h | .2 C₆H₅—SO₃H | 48° |
| 10i | .2 DBA | 55° |
| 10k | .2 H₂NSO₃H | 40° |
| 10l | .2 Camphorsulfonic acid | 78° |
| 10m | .2 C₁₄H₂₉SO₃H | oil |
| 10n | .DNND | 108° |

-continued

| Salt No. | Formula | Softening or melting point |
|---|---|---|
| 10p | .NND | oil |
| 11 | C₆H₅CH₂—N⟨piperidinyl⟩—OOC—(CH₂)₇—COO—⟨piperidinyl⟩N—CH₂C₆H₅.2 MMP | resin |
| 11a | .MPA | oil |
| 11b | .2 TSA | 105° |
| 12 | HN⟨piperidinyl⟩—OOC—(CH₂)₈—COO—⟨piperidinyl⟩NH.TSA | resin |
| 12a | .2 TTA | 250° |
| 12b | .MPA | 250° (sublimation) |
| 12c | .2 MMP | 250° (sublimation) |
| 12d | .2 C₄H₉OOC—CH=CH—COOH | 110° |
| 12e | .2 C₆H₁₃OOC—CH=CH—COOH | 90° |
| 12f | .C₆H₅—P(O)(OH)₂ | 80° |
| 12g | .DNND | 160° |
| 13 | CH₃—N⟨piperidinyl⟩—OOC—(CH₂)₈—COO—⟨piperidinyl⟩N—CH₃.DBA | oil |
| 13a | .2 DBA | liquid |
| 13b | .TSA | 50° |
| 13c | .2 TSA | 75° |
| 13d | .2 MPA | resin |
| 13e | .2 C₁₄H₂₉SO₃H | liquid |
| 13f | .C₆H₅P(O)(OH)₂ | 80° |
| 14 | C₆H₅CH₂—N⟨piperidinyl⟩—OOC—(CH₂)₈—COO—⟨piperidinyl⟩N—CH₂C₆H₅.2 TSA | 100° |
| 14a | .2 MMP | 98° |
| 14b | .2 PSA | resin |
| 14c | .2 DBA | 62° |
| 14d | .DNND | 120° |
| 14e | .2 Vinylsulfonic acid | 160° |
| 14f | .NND | visc. oil |
| 14g | .1,9 TSA | 90° |
| 14h | .1,8 TSA | 90° |
| 14i | .1,7 TSA | 88° |
| 15 | CH₂=CHCH₂—N⟨piperidinyl⟩—OOC—(CH₂)₈—COO—⟨piperidinyl⟩N—CH₂CH=CH₂.2 TSA | 95° |
| 15a | .DNND | 104° |
| 15b | .2 DBA | 44° |
| 15c | .NND | visc. oil |
| 15d | .2 C₄H₉OOC—CH=CH—COOH | 50° |
| 15e | .2 MSA | 78° |

-continued

| Salt No. | Formula | Softening or melting point |
|---|---|---|
| 16 | CH₃—N(piperidine)—NH—C₄H₉·MPA | 130° |
| 16a | .2 MMP | 95° |
| 17 | HO—(piperidine)—N—CH₂CH=CHCH₂—N—(piperidine)—OH·MPA | 205° |
| 17a | .2 MMP | 170° |
| 18 | HO—(piperidine)—N—CH₂—(C₆H₄)—CH₂—N—(piperidine)—OH·MPA | 250° |
| 18a | .2 MMP | 55° |
| 19 | HOOC—CH(C₈H₁₇)—CH₂—COO—(piperidine)—N—CH₂—(C₆H₄)—CH₂—N—(piperidine)—OOC—CH₂—CH(C₈H₁₇)—COO·2 MMP | 20° |
| 19a | .MPA | 60° |
| 19b | .2 TSA | 105° |
| 20 | HOOC—CH(C₈H₁₇)—CH₂—COO—(piperidine)—N—CH₂—CH=CHCH₂—N—(piperidine)—OOC—CH₂—CH(C₈H₁₇)—COOH·2 TSA | 96° |
| 20a | .2 MMP | 50° |
| 21 | HOOC—CH(C₁₂H₂₅)—CH₂—COO—(piperidine)—N—CH₂CH=CHCH₂—N—(piperidine)—OOC—CH₂—CH(C₁₂H₂₅)—COOH·MPA | 65° |
| 21a | .2 MMP | resin |

| Salt No. | Formula | Softening or melting point |
|---|---|---|
| 22 | (structure with piperidine rings, CH₃—N, COO linker, N—CH₃·2 TSA) | 138° |
| 23 | (structure with piperidine rings, CH₃—N, COO—(CH₂)₈—OOC linker, N—CH₃·2 TSA) | 95° |
| 24 | (triazine-like structure with three piperidine rings bearing C₄H₉ groups, NH·TSA) | 150° |
| 24a | .DBA | 92° |
| 24b | .2 DBA | 96° |
| 24c | .3 DBA | 102° |
| 24d | .MPA | 250° |
| 24e | .1½ MPA | 215° |
| 24f | .1½ DNND | >250° |
| 25 | (analogous structure with C₁₂H₂₅ groups, NH·TSA) | 50° |
| 25a | .2 TSA | 260° |
| 25b | .3 TSA | 300° |
| 26 | $+CH-CH_2\frac{}{}_n$ .n TSA, with C=O, O, piperidine bearing N—CH₃ | 140° |
| 26a | . n DBA | 96° |
| 27 | (polymer structure with piperidine—O—...—N—CH₂—CH₂—OOC—CH₂CH₂—CO—)$_n$ .n TSA | 135° |

| Salt No. | Formula | Softening or melting point |
|---|---|---|
| 28 | [−O−⟨piperidine⟩−N−CH₂−CH(CH₃)−OOC−(CH₂)₇−CO−]ₙ · n TSA | 115° |
| 29 | C₆H₅CH₂−N⟨piperidine⟩−OOC−CH(CH₃)−CH₂−C(CH₃)₂−CH₂−COO−⟨piperidine⟩N−CH₂C₆H₅ · 2 TSA | 90° |
| 30 | [−O−⟨piperidine⟩−N−CH₂CH₂−OOC−C(C₂H₅)₂−CO−]ₙ · (n/2) DNND | 250° |
| 30a | .n TSA | 145° |
| 31 | CH₃−N⟨piperidine⟩(NH−C=O, C=O−N−C₄H₉) .TSA | 90° |
| 32 | HN⟨piperidine⟩(NH−C=O, C=O−N−C₁₂H₂₅) .CH₃SO₃H | 210 to 18° |
| 33 | C₆H₅CH₂−N⟨piperidine⟩(NH−C=O, C=O−N−C₁₂H₂₅) .TSA | 102° |
| 34 | HN⟨piperidine⟩(NH−C=O, O−(CH₂)₁₁−ring) .TSA | 230° |
| 35 | NCCH₂−N⟨piperidine⟩−OOC−(CH₂)₈−COO−⟨piperidine⟩N−CH₂CN · 2 TSS | 105° |
| 36 | NCCH₂−N⟨piperidine⟩−OCC−CH₂CH₂OCH₂CH₂−COO−⟨piperidine⟩N−CH₂CN · 2 TSS | 114° |

-continued

| Salt No. | Formula | Softening or melting point |
|---|---|---|
| 37 | C₆H₅—CH₂—N(piperidine)—OOC—NH—(CH₂)₆—NH—COO—(piperidine)N—CH₂—C₆H₅ . 2 MSS | 132° |
| 38 | CH₃—N(piperidine with CH₃, C₂H₅, CH₃, C₂H₅ substituents)—OH.CH₃SO₃H | 60° |
| 39 | HN(piperidine)—OOC—C₆H₅.CH₂=CH—CONH—C(CH₃)₂—CH₂—SO₃H | 71° |
| 39a | .C₈H₁₇—P(O)(OC₂H₅)OH | 65° |
| 39b | .C₁₈H₃₇—P(O)(OC₂H₅)OH | 54° |
| 40 | CH₃—N(piperidine)—OOC—C₆H₅.CH₂=CH—SO₃H | 71° |

Preparation of inner salts of piperidinesulfonic acids 13.58 g (0.06 mol) of 1,2,2,6,6-pentamethyl-4-n-butylaminopiperidine and 7.3 g (0.06 mol) of propanesultone are heated in 80 ml of anhydrous xylene for 21 hours at 100° with stirring and in an N₂ atmosphere. On cooling to room temperature there is formed a precipitate, which is separated, dissolved in a small amount of dichloromethane, and again precipitated by being poured into 500 ml of 2-butanone at about 0° with stirring. The precipitate is filtered off, subsequently washed in a small amount of diethyl ether and dried in vacuo to thus obtain, in the form of inner salt (betain), the sulfonic acid of the following structure

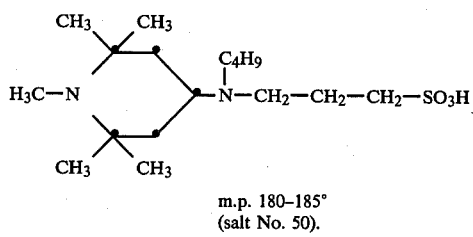

m.p. 180–185°
(salt No. 50).

There is obtained in an analogous manner, from 14.1 g (0.05 mol) of 1,2,2,6,6-pentamethyl-4-n-octylaminotetramethylpiperidine and 6.11 g (0.05 mol) of propanesultone in 80 ml of dioxane, in the form of inner salt, the sulfonic acid of the following structure

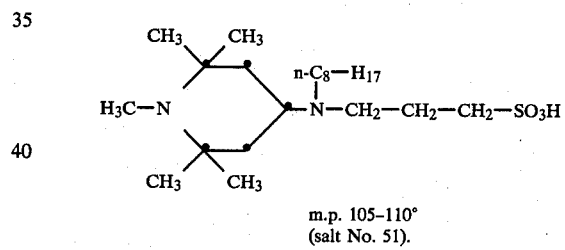

m.p. 105–110°
(salt No. 51).

In an analogous manner, 13 g (0.07 mol) of 1-(2-hydroxyethyl)-2,2,6,6-tetramethylpiperidine are reacted at 110°–115° with 8.55 g (0.07 mol) of propanesultone. After cooling to about 0°–5°, the white precipitate is filtered off, and then washed with diethyl ether. The precipitate is subsequently dissolved in 30 ml of chloroform, and this solution is poured, with vigorous centrifuging, into 400 ml of a diethyl/acetone mixture (3:1). The white precipitate is filtered off with suction and dried in high vacuum. The resulting sulfonic acid of the structure

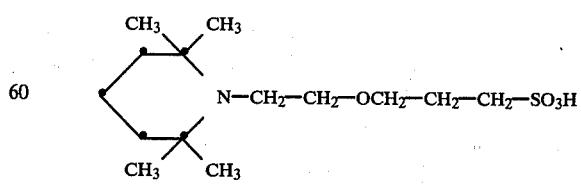

melts at 235°–240° (salt No. 52).

The amount of polyalkylpiperidine salt required of curing the lacquers depends on the nature of the lacquer resin and also on the curing temperature. In general, about 0.1 to 5% by weight of piperidine salt are used, based on the solvent-free lacquer resin, and preferably 1-2%, by weight are used. With these amounts, an adequate light stabilising action of the piperidine salts is also ensured. The salt is added to the lacquer by simple mixing with the other components of the lacquer. The salt can also be added in the form of a solution to the lacquer. This is of advantage especially when the salt is obtained in the form of a solution from its preparation, so that it is not necessary to isolate the salt.

In addition to the lacquer resin, the lacquers usually contain an organic solvent or solvent mixture, but they can constitute an aqueous solution or dispersion or can be solvent-free. Lacquers with a low solvent content, so-called "high solids lacquers", are of particular interest. The lacquers can be clear lacquers such as are used, for example, in the automobile industry as top-coat lacquers of multi-coat paintwork. They can also contain pigments, which can be inorganic or organic pigments or also metal pigments for metal-effect lacquers.

The lacquers can also contain relatively small amounts of specific additives which are customary in lacquer technology, for example flow improvers, thixotropic agents or antioxidants. Although the piperidine salts which can be used according to the invention are outstanding light stabilisers, it can be advantageous in specific cases additionally to use yet further light stabilisers, for example those of the UV-absorber type or of the organic nickel compound type, because synergistic effects can then arise. Examples of categories of UV absorbers which can be used are the hydroxyphenylbenztriazoles, the hydroxybenzophenones, the oxanilides, the cyanoacrylates and the hydroxyphenyl-s-triazines. Examples of organic nickel compounds are nickel salts of phosphonic acid monoesters or Ni complexes of bis-phenols. The additional use of hydroxyphenyl-benztriazole light stabilisers, for example of 2-(2-hydroxy-3,5-di-t-amylphenyl)-benztriazole or 2-[2-hydroxy-3,5-di-($\alpha$-dimethylbenzyl)-phenyl]-benztriazole, is particularly preferred.

The lacquers are applied by the conventional methods for industrial lacquer-coating to the substrates to be coated, for example by spreading, spraying or dipping.

After application, the lacquers are dried and stoved. The curing temperature can be 80° to 300° C., with curing times of a few seconds up to one hour. Low curing temperatures of about 100° to 150° C., such as are employed for repair paintwork on automobiles or other types of lacquer coating of sensitive industrial articles, are of particular interest for the process according to the invention.

The process according to the invention is suitable for all types of industrial lacquer coating, for example for the lacquer coating of machines, vehicles, ships or structural parts. It is of particular importance for vehicle paintwork. In this case, it can be used either in one-coat paintwork or in multi-coat paintwork. The use of the process for the continuous coating of sheet metal, for example sheet steel or aluminium, i.e. the so-called coil-coat process, is also of particular interest.

In the test which follows, the process according to the invention is described in more detail with the aid of several typical examples. In these examples, parts and % are by weight. The temperatures are in °C.

EXAMPLE 1:

A clear lacquer is prepared by mixing the following constituents: 53.7 parts of an acrylic resin containing a hydroxyl functional group (Paraloid OL 42, Rohm & Haas Corp., USA), 19.2 parts of hexamethoxymethylmelamine (Cymel 301, Amer. Cyanamid, USA), 1.9 parts of cellulose acetobutyrate (CAB 551.001, Eastman Chem. Corp., USA), 2.9 parts of a flow improver based on silicone (Byketol Special, Byk-Mallinckrodt GmbH), 0.3 part of a flow improver based on a surfactant in the form of a 1% solution in ethylglycol acetate (Modaflow, Monsanto-Corp.), 10.5 parts of n-butanol and 11.5 parts of butyl acetate.

This clear lacquer has a solids content of 63%. The amounts of curing catalysts indicated in Table 1 are added to this clear lacquer.

The lacquer samples are applied to glass plates in a coating thickness (wet) of 50 $\mu$m and cured for 30 minutes in a drying cabinet at the temperature indicated in Table 1. The resulting lacquer films have a layer thickness of about 30 $\mu$m. After storing for 60 minutes in standard atmospheric conditions (23° C./50% relative atmospheric humidity), the pendulum hardness of the lacquer films is measured using Koenig's method (DIN 53,157). The results are summarised in Table 1.

TABLE 1

| Curing catalyst and amount added(*) | Curing temperature and curing time | Pendulum hardness by the Koenig method (seconds) |
|---|---|---|
| without | 150°/30 minutes | tacky |
| Salt No. 1a | | |
| 1% | " | 98 |
| 0.5% | " | 31 |
| Salt No. 9c 1% | " | 130 |
| Salt No. 10 | | |
| 1% | " | 156 |
| 0.5% | " | 148 |
| 0.5% | 130°/30 minutes | 114 |
| 0.5% | 120°/30/minutes | 67 |
| Salt No. 14 | | |
| 1% | 150°/30 minutes | 163 |
| 0.5% | " | 155 |
| 0.5% | 130°/30 minutes | 107 |
| 0.5% | 120°/30 minutes | 91 |
| Salt No. 3 1% | 150°/30 minutes | 130 |
| No. 9 1% | " | 97 |
| No. 9c 1% | " | 130 |
| No. 10d 1% | " | 140 |
| No. 10m 1% | " | 140 |
| No. 15a 1% | " | 135 |
| without | " | tacky |
| Salt No. 17 1% | " | 109 |
| No. 19a 1% | " | 81 |
| No. 27 1% | " | 94 |

(*)based on the solids content of the lacquer

EXAMPLE 2

The clear lacquer described in Example 1 is used as the top-coat lacquer in two-coat metal-effect paintwork, such as is customary in the automobile industry.

For this purpose 0.4 mm thick aluminium sheets are pre-treated with a commercially available primer and coated with a commercially available filler based on an epoxide/polyester stoving lacquer.

A silver-coloured base lacquer is applied on top of this, the base lacquer having the following composition: 27 parts of a heat-curable polyester resin (Polyester L 1850, Dynamit Nobel AG, Federal Republic of Germany), 3 parts of a melamine resin (Maprenal RT, Hoechst AG, Federal Republic of Germany), 2 parts of a cellulose acetobutyrate (CAB 531, Eastman Chem. Corp.), 8 parts of aluminium pigment (Alcoa 726, Aluminium Corp, USA), 10 parts of toluene, 7 parts of xylene, 3 parts of butanol, 25 parts of butyl acetate and 15 parts of a mixture of aromatic solvents (Solvesso 100, Esso AG).

The base lacquer is sprayed on in a coating thickness of about 15 μm (wet), and the clear lacquer is sprayed wet-in-wet onto this in a coating thickness of about 30–40 μm. After exposing to the air for a short time, the lacquer is stoved in a drying oven for 30 minutes at 150°. The thickness of the dry film is about 40 μm. After storing for 2 weeks in standard atmospheric conditions (23° C./50% relative atmospheric humidity), the samples are weathered in a rapid weathering apparatus in accordance with ASTM G 53-77. For comparison, a sample is catalysed with p-toluenesulfonic acid with additional light stabiliser.

The gloss according to ASTM D No. 523 (20° gloss) is used as the criterion for the stabilising effect. The results are given in Table 2.

TABLE 2

| Curing catalyst | 20° gloss unweathered | weathered for 400 hours |
|---|---|---|
| Salt No. 10 0.5% | 85 | 59 |
| Salt No. 14 0.5% | 83 | 56 |
| Toluenesulfonic acid 0.5% | 86 | 36 |

EXAMPLE 3

The curing catalysts according to the invention which are listed in Table 3 are added, in each case in an amount of 1% by weight (based on solids) to the clear lacquer described in Example 1 and the lacquer samples are applied to glass plates as described in Example 1. Curing is effected for 30 minutes at 150° C. After storing for 24 hours in standard atmospheric conditions (23° C./50% relative atmospheric humidity), the pendulum hardness is measured by the Koenig method (DIN No. 53,157).

In addition, in order to determine the storage stability of each catalysed lacquer sample, the viscosity is measured after storing for 0, 10, 20, 30, 40 and 50 days at room temperature, using a cone-and-plate viscometer according to DIN No. 53,229. The $T_{40}$ value given in Table 3 indicates the time in days after which the viscosity of the lacquer has risen by 40%

TABLE 3

| Curing catalyst (1% in each case) | Pendulum hardness by the Koenig method (seconds) | $T_{40}$ (days) |
|---|---|---|
| p-Toluenesulfonic acid | 160 | 5 |
| Salt No. | | |
| 4 | 164 | 44 |
| 5 | 174 | 47 |
| 6b | 167 | 43 |
| 6c | 170 | 41 |
| 6d | 154 | 40 |
| 10 | 165 | 39 |
| 10c | 172 | 47 |
| 10e | 169 | 36 |
| 10f | 159 | 40 |
| 10g | 170 | 50 |
| 10h | 164 | 38 |
| 10k | 162 | 41 |
| 10l | 167 | 42 |
| 13c | 148 | 39 |
| 15 | 161 | 31 |
| 20 | 168 | 34 |
| 22 | 160 | 42 |

TABLE 3-continued

| Curing catalyst (1% in each case) | Pendulum hardness by the Koenig method (seconds) | $T_{40}$ (days) |
|---|---|---|
| 23 | 148 | 37 |
| 26 | 148 | 42 |
| 26a | 159 | 47 |
| 29 | 163 | 42 |

These results show that, in respect of their catalytic activity, the piperidine salts according to the invention have an effect which is not inferior to that of toluenesulfonic acid, but a considerably longer pot life is achievable.

What is claimed is:

1. A process for curing acid curable stoving lacquers by warming in the presence of a curing catalyst, wherein the curing catalyst used is either (a) an acid addition salt of a basic polyalkylpiperidine derivative which contains a group of the formula I

in which R is hydrogen or methyl, and an inorganic or organic acid, or (b) the inner salt of a sulfonic acid which contains a group of the formula I.

2. A process according to claim 1, wherein the curing catalyst used is an acid addition salt of a mono- or polysulfonic acid, of an acid phosphoric acid ester, of a phosphonic acid or a monoester thereof, of maleic acid or a monoester thereof or of phthalic acid or a monoester thereof.

3. A process according to claim 2, wherein the curing catalyst used is a salt of a basic polyalkylpiperidine derivative which contains a group of the formula I, in which R is hydrogen, with a mono- or di-sulfonic acid.

4. A process according to claim 1, wherein the curing catalyst used is an acid addition salt of a basic polyalkylpiperidine derivative, which contains a group of the formula Ia

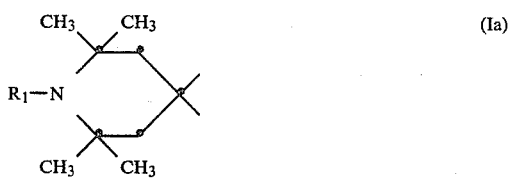

in which $R_1$ is $C_1$–$C_4$ alkyl, cyanomethyl, $C_3$–$C_5$ alkenyl or $C_7$–$C_9$ aralkyl.

5. A process according to claim 4, wherein $R_1$ is allyl or benzyl.

6. A process according to claim 2, wherein a salt is used which contains the same number of base equivalents as acid equivalents or contains a slight excess of base equivalents.

7. A process according to claim 2, wherein the curing catalyst used is the inner salt of a sulfonic acid of one of the following formulae

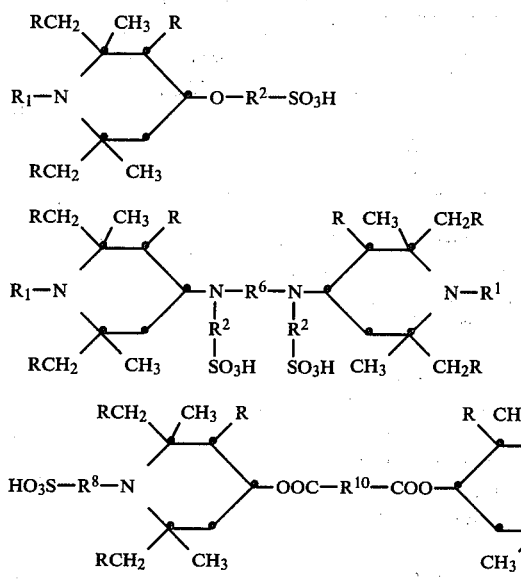

in which R is hydrogen or methyl, R¹ is hydrogen, $C_1$-$C_{12}$ alkyl, $C_3$-$C_8$ alkenyl, $C_3$-$C_8$ alkynyl, $C_7$-$C_{12}$ aralkyl or —$CH_2CN$, $R^2$ is a —$(CH_2)_3$— or —$CH_2$—$CH(R^3)$—CONH—$R^4$ group, in which $R^3$ is hydrogen or methyl and $R^4$ is $C_2$-$C_8$ alkylene, $R^5$ is $C_1$-$C_{12}$ alkyl, $C_5$-$C_7$ cycloalkyl or $C_7$-$C_9$ aralkyl, $R^6$ is $C_2$-$C_{12}$ alkylene, $C_4$-$C_{10}$ alkylene which is interrupted by —O—, $C_6$-$C_{15}$ cycloalkylene or xylylene, $R^7$ is $C_1$-$C_{18}$ alkyl, $C_6$-$C_{12}$ aryl or alkaryl, $C_7$-$C_{12}$ aralkyl or an $R^{11}$—NH—group, $R^8$ is —$(CH_2)_3$— or —$CH_2$—$CH(R^9)$—O—$(CH_2)_3$—, $R^9$ is hydrogen, methyl, phenyl, phenoxymethyl or tolyloxymethyl, $R^{10}$ is $C_2$-$C_{12}$ alkylene, $C_2$-$C_{12}$ alkylene interrupted by —O—, $C_6$-$C_{12}$ arylene, $C_6$-$C_{12}$ cycloalkylene or an —NH—$R^{12}$—NH—group, $R^{11}$ is $C_1$-$C_{18}$ alkyl, cyclohexyl, $C_6$-$C_{12}$ aryl or $C_7$-$C_9$ aralkyl and $R^{12}$ is $C_2$-$C_{12}$ alkylene, $C_6$-$C_{14}$ arylene or $C_6$-$C_{12}$ cycloalkylene.

8. A process according to claim 7, wherein the inner salt of a sulfonic acid of the formula II or III is used in which $R^1$ is methyl, allyl or benzyl and $R^2$ is a —$(CH_2)_3$ group.

9. A process according to claim 1, wherein the curing catalyst is used in an amount of 0.1 to 5% by weight and preferably of 1 to 2% by weight, based on the solvent-free lacquer resin.

10. A process according to claim 1, wherein the lacquer is cured at 80° to 300° C. and preferably at 100° to 150° C.

* * * * *